United States Patent [19]
Hess et al.

[11] Patent Number: 5,584,802
[45] Date of Patent: Dec. 17, 1996

[54] ELASTIC KNEE-JOINT BANDAGE

[75] Inventors: Heinrich Hess, Saarlouis; Wolfgang Krause, Kassel; Hans B. Bauerfeind, Kempen, all of Germany

[73] Assignee: Bauerfeind GmbH and Co., Germany

[21] Appl. No.: 532,841

[22] PCT Filed: Mar. 28, 1994

[86] PCT No.: PCT/EP94/00979

§ 371 Date: Oct. 6, 1995

§ 102(e) Date: Oct. 6, 1995

[87] PCT Pub. No.: WO94/22404

PCT Pub. Date: Oct. 13, 1994

[30] Foreign Application Priority Data

Apr. 7, 1993 [DE] Germany .................. 43 11 500.4

[51] Int. Cl.[6] ......................................... A61F 5/00
[52] U.S. Cl. ................................. 602/62; 602/26
[58] Field of Search .................. 602/61–63, 20, 602/23, 26; 2/22, 23, 24

[56] References Cited

U.S. PATENT DOCUMENTS

| | | | |
|---|---|---|---|
| 2,068,173 | 10/1934 | Galves | 602/62 X |
| 3,831,467 | 8/1974 | Moore | 602/62 X |
| 3,888,244 | 6/1975 | Lebold | 602/62 X |
| 4,084,584 | 4/1978 | Detty | 602/63 X |
| 4,120,052 | 10/1978 | Butler | 2/24 X |

*Primary Examiner*—Richard J. Apley
*Assistant Examiner*—David R. Risley

[57] ABSTRACT

An elastic knee support is designed as a flexible tube (5) with an elastic profiled insert (6) in the area of the hollow of the knee. The profiled insert extends across the axis of the leg, covering the sinews (11,12) of the hollow of the knee. Recesses (7,8) which receive each one sinew of the hollow of the knee interrupt on both sides of the sinews of the hollow of the knee supporting zones of the profiled insert which exercise a pressure on the hollow of the knee.

3 Claims, 2 Drawing Sheets

5,584,802

ELASTIC KNEE-JOINT BANDAGE

The invention relates to a knee-joint bandage in the form of a tube with an elastic profiled insert in the region of the back of the knee.

BACKGROUND OF THE INVENTION

Elastic knee-joint bandages with profiled inserts are used, on the one hand, to protect the knee in particular against sports accidents and also to support the injured knee, it being necessary for the knee-joint bandage to surround the knee joint in such a manner that the normal mobility of the knee joint is not decisively impaired while, however, false movements and false position of the knee joint are largely prevented. In any case, when the knee is bent, the knee-joint bandage is compressed in the region of the popliteal space or back of the knee, respectively this leading in particular to folds in the bandage which cause pain to the wearer.

DESCRIPTION OF THE PRIOR ART

An elastic knee-joint bandage with a profiled insert surrounding the knee cap is disclosed, for example, in DE-PS 39 91 334.

In order to reduce or to prevent folding of the knee-joint bandage in the region of the knee joint, knee-joint bandages have already been made in the knee-joint region from particularly loosely woven or thin textile material. It is known from U.S. Pat. No. 4,651,722 to leave the entire popliteal region exposed.

It has now been demonstrated that it is medically desirable to provide elastic profiled inserts also in the popliteal region, in order to obtain an intermittent massage effect in said region.

A knee-joint bandage serving to protect the knee joint against sports accidents, with four profiled inserts cushioning the knee joint at the sides thereof as well as at the front and back thereof, is known from U.S. Pat. No. 3,375,821. In said knee-joint bandage, the two lateral profiled inserts and the front profiled insert are joined together, whereas the profiled insert protecting the popliteal space is not connected to the two lateral profiled inserts. Said profiled insert is left with a certain freedom of mobility, apparently in order thereby to provide the bandage with sufficient flexibility and in order, when the knee is bent, to absorb ensuing folds in the manner of a cushion.

SUMMARY OF THE INVENTION

The object of the invention is to create an elastic elongated, knee-joint bandage with an elastic profiled insert, said knee-joint bandage being distinguished in that it does not cause any pain to the wearer during constantly repeated bending of the knee, while, however, also giving rise to the intermittent massage effect. According to the invention this is achieved in that the profiled insert, extending transversely with respect to the axis of the leg, reaches so far beyond the popliteal tendons that support regions of the profiled insert - said support regions exerting a pressure on the popliteal space - are interrupted on either side of the popliteal tendons (11, 12) by recesses, or grooves extending along the axis of the leg in the profioled insert and each accommodating one popliteal tendon.

During the testing of this knee-joint bandage, it has been demonstrated that the recesses accommodating the popliteal tendons leave sufficient space when the knee is bent, such that the profiled insert is unable, in the region of the popliteal space, to exert any pressure on the popliteal tendons. However, the desired therapeutic effect of and emanating from the elastic profiled insert is fully maintained, since said profiled insert is able, to exert pressure on the popliteal space, adjacent to the recesses, albeit without exerting pressure on the protruding popliteal tendons.

The hereinbefore-described design of the elastic knee-joint bandage according to the invention may be employed irrespective of whether the knee-joint bandage is provided with profiled inserts also in the region of the sides of the knee or additionally in the region of the knee cap.

It is advantageous for the specially shaped insert to be loosely positioned between the tube and an elastic textile covering extending across the profiled insert and the edge thereof being elastically connected to the tube. This design permits the simple manufacture of the knee-joint bandage, the profiled insert being sufficiently held in position by the elastic covering. The elastic covering can then be connected by its edge to the tube either by bonding or by sewing. Such a connection can be made elastically, either by means of an elastic glue or by means of an elasticity-permitting seam.

In order to provide the knee-joint bandage with good adhesion on the knee, it is advantageous for the covering to be provided with at least one window, directed towards the knee, for the profiled insert to contact the skin. In this case, owing to its surface, the profiled insert effects good adhesion on the skin, especially if the profiled insert is made of silicone rubber.

It should additionally be pointed out that it is, of course, also possible to use other materials for making the profiled insert, particularly foam rubber, pads with air inclusions, profiled pads with tooth-like notches for the facilitation of bending and similar.

BRIEF DESCRIPTION OF THE DRAWINGS

Embodiments of the invention are represented in the drawings, in which:

FIG. 2 shows a section through the arrangement according to

FIG. 1 along line II—II from FIG. 1; and

DETAILED DESCRIPTION OF THE PREFERRED EMBODIMENTS

Figure 1:
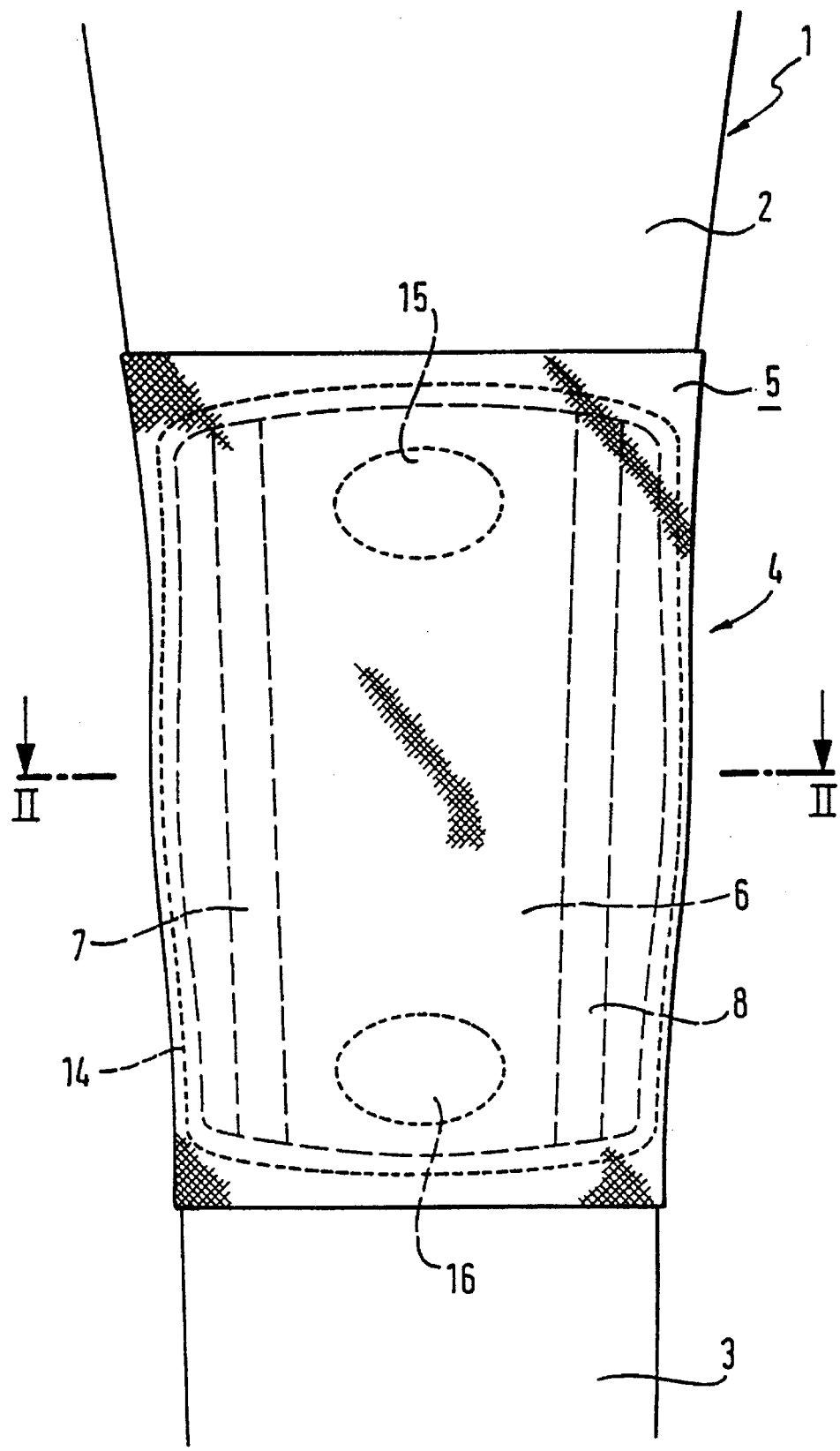
FIG. 1 shows the view of a knee joint with popliteal space facing the observer, with fitted knee-joint bandage.

FIG. 1 shows section by section a human leg 1 with the thigh 2 and the lower leg 3, with the knee joint 4 situated therebetween. The leg 1 represented in the drawing shows the observer the side with the popliteal space 10 (see FIG. 2). The elastic knee-joint bandage in the form of an elongated tube 5 made an elastic textile material, has been pulled over the leg 1. Inserted into the knee-joint bandage 5 on the popliteal-space side thereof facing the observer is the elastic profiled insert 6, which profiled insert 6 is provided with the two recesses or grooves 7 and 8, the purpose of which two recesses 7 and 8 is, when the knee 4 is bent, to accommodate the tendons on either side of the popliteal space (see FIG. 2). The covering 13 shown in FIG. 2 for enclosing the elastic profiled insert 6, of which covering 13 only the edge 14 is shown in FIG. 1, is provided on the side facing towards the knee joint 4 with the two windows 15 and 16, which allow contact between the elastic profiled insert 6 and the skin of the knee joint 4. This creates a certain adhesion of the profiled insert 6 on the skin of the knee joint 4, which permits slide-free wearing of the knee-joint bandage.

Figure 2:
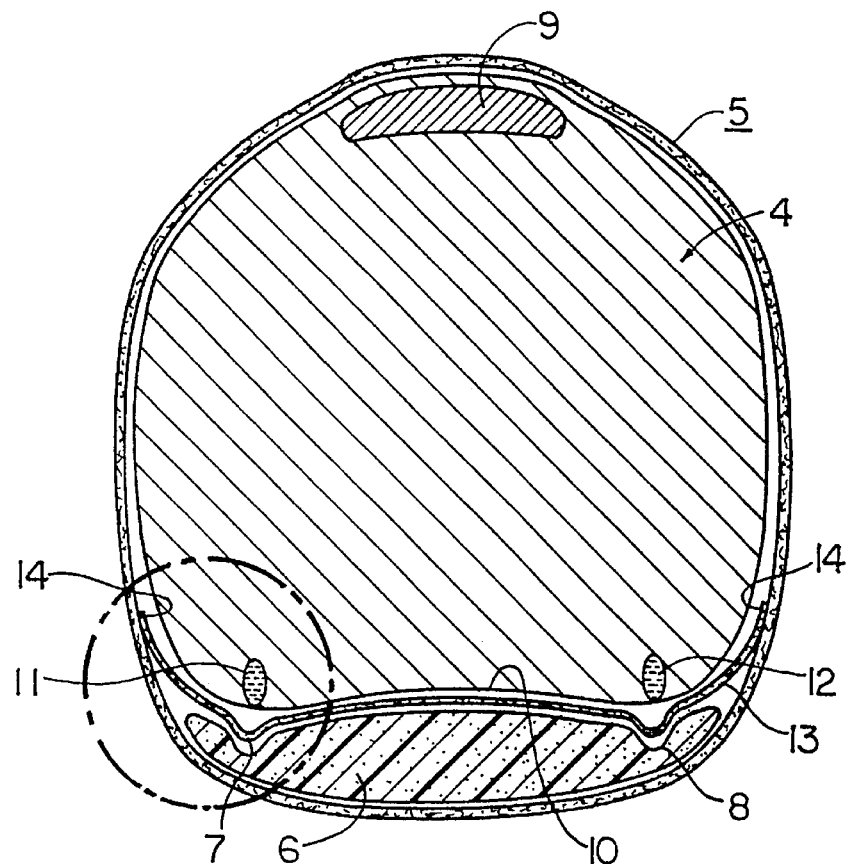

The section shown in FIG. 2 along line II—II from FIG. 1 shows the knee joint 4, the knee-joint bones having been omitted in this representation. The drawing shows only the knee cap 9. The two knee-joint tendons 11 and 12 extend on either side of the popliteal space 10. Pulled over the knee joint 4 is the tube 5, which is fitted on the side of the popliteal space 10 with the elastic covering 13. Said elastic covering 13 may be made of the same textile material as the tube 5. The covering 13 is elastically connected—in this case by bonding—to the tube 5 along the edge 14 of the covering 13. In conjunction with the tube 5, the covering 13 thus forms a pocket enclosing the elastic profiled insert 6. The representation in FIG. 2 shows a small gap between the skin of the knee joint 4 and the tube 5, which gap does not, of course, exist—owing to the elasticity of the tube—when the tube has been pulled over the knee joint. In practice, therefore, the tube directly rests on contact with the skin of the knee joint 4. In FIG. 2, said gap is provided only for reasons of clarity of the representation.

Opposite the tendons 11 and 12, the elastic profiled insert 6 comprises the recesses 7 and 8, into which, when the knee 4 is bent, the tendons 11 and 12 move and are consequently accommodated in virtually pressureless and therefore pain-free manner by the recesses 7 and 8. In this way, however, the regions laterally adjacent to the recesses 7 and 8 exert a desired pressure on the popliteal space 10. In the representation shown in FIG. 2 with the knee 4 extended, the tendons 11 and 12 are shown, according to their then prevailing position, with a distance from the two recesses 7 and 8.

Figure 3:
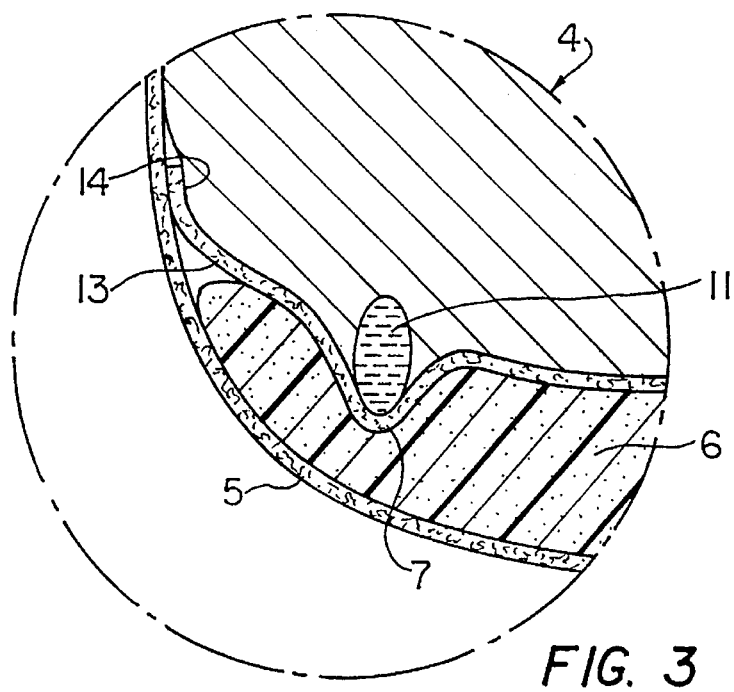
FIG. 3 shows a detail from FIG. 2.

FIG. 3 shows the encircled region of FIG. 2, in this case with the knee joint bent. With the knee joint in this position, the knee-joint tendon 11 (the same applies also, of course, to the knee-joint tendon 12 not shown) pops out of the relevant region of the leg and is accommodated by the recess 7, with the result that the skin surrounding the knee-joint tendon 11 is not subjected to any pressure whatsoever from the elastic profiled insert 6. However, the regions of the elastic specially shaped insert 6 adjacent to the recess 7 are used to exert pressure against the regions of the knee joint adjacent to the knee-joint tendon 11, this resulting in the hereinbefore-mentioned desired massage effect.

What is claimed is:

1. An elastic knee-joint bandage, comprising:

an elongated tube constructed of an elastic material; and an elastic profiled insert positioned inside the elongated tube and extending along the length of the popliteal space, the insert having a pair of parallel preformed grooves extending along the entire length of the insert such that when the bandage is placed about the knee, the insert is positioned over the popliteal space, each groove accommodating one popliteal tendon, whereby the insert exerts pressure on the popliteal space without exerting pressure on the popliteal tendons.

2. Knee-joint bandage according to claim 1, characterized in that the profiled insert (6) is loosely positioned between the tube (5) and an elastic textile covering (13), said elastic textile covering (13) extending across the profiled insert (6) and the edge (14) thereof being elastically connected to the tube (5).

3. Knee-joint bandage according to claim 1, characterized in that the covering (13) is provided with at least one window (15, 16), directed towards the knee joint (4), for the profiled insert (6) to contact the skin.

\* \* \* \* \*